(12) United States Patent
Ding

(10) Patent No.: US 10,751,110 B2
(45) Date of Patent: *Aug. 25, 2020

(54) BIPOLAR SURGICAL INSTRUMENT WITH TISSUE STOP

(71) Applicant: COVIDIEN LP, Mansfield, MA (US)

(72) Inventor: Weijiang Ding, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/907,185

(22) PCT Filed: Aug. 7, 2013

(86) PCT No.: PCT/CN2013/080954
§ 371 (c)(1),
(2) Date: Jan. 22, 2016

(87) PCT Pub. No.: WO2015/017995
PCT Pub. Date: Feb. 12, 2015

(65) Prior Publication Data
US 2016/0157923 A1 Jun. 9, 2016

(51) Int. Cl.
*A61B 18/14* (2006.01)
*A61B 17/28* (2006.01)
*A61B 18/00* (2006.01)

(52) U.S. Cl.
CPC ...... *A61B 18/1442* (2013.01); *A61B 17/2812* (2013.01); *A61B 2017/2829* (2013.01);
(Continued)

(58) Field of Classification Search
CPC .... A61B 2017/2829; A61B 2017/2948; A61B 18/1442; A61B 18/1452; A61B 18/1455
See application file for complete search history.

(56) References Cited

U.S. PATENT DOCUMENTS

D249,549 S   9/1978  Pike
D263,020 S   2/1982  Rau, III
(Continued)

FOREIGN PATENT DOCUMENTS

CN   201299462       9/2009
DE   2415263 A1    10/1975
(Continued)

OTHER PUBLICATIONS

U.S. Appl. No. 08/926,869, filed Sep. 10, 1997, James G. Chandler.
(Continued)

*Primary Examiner* — Jaymi E Della
*Assistant Examiner* — Sean W Collins

(57) ABSTRACT

A bipolar forceps includes a mechanical forceps including first and second shafts each having a jaw member extending from a distal end thereof and a handle disposed at a proximal end thereof for effecting movement of the jaw members relative to one another about a pivot. A disposable is housing is configured to be releasably coupled to at least one of the shafts and an electrode assembly is configured to be releasably coupled to the disposable housing. The electrode assembly includes electrodes releasably coupled to the jaw members. At least one of the electrodes includes a knife channel configured to receive a knife blade therethrough to cut tissue grasped between the jaw members. A tissue stop has a knife slot that aligns with the knife channel to receive the knife blade. An actuation mechanism advances the knife blade through the knife channel to cut tissue.

11 Claims, 10 Drawing Sheets

(52) U.S. Cl.
CPC ............... *A61B 2018/0063* (2013.01); *A61B 2018/00601* (2013.01); *A61B 2018/1455* (2013.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| 5,304,203 A | 4/1994 | El-Mallawany et al. | |
| D348,930 S | 7/1994 | Olson | |
| D349,341 S | 8/1994 | Lichtman et al. | |
| 5,358,506 A * | 10/1994 | Green | A61B 17/29 227/181.1 |
| D354,564 S | 1/1995 | Medema | |
| D358,887 S | 5/1995 | Feinberg | |
| 5,499,998 A * | 3/1996 | Meade | A61B 17/29 606/207 |
| 5,578,052 A | 11/1996 | Koros et al. | |
| 5,618,294 A | 4/1997 | Aust et al. | |
| D384,413 S | 9/1997 | Zlock et al. | |
| 5,665,100 A | 9/1997 | Yoon | |
| H1745 H | 8/1998 | Paraschac | |
| 5,800,449 A * | 9/1998 | Wales | A61B 18/1447 606/170 |
| 5,814,043 A | 9/1998 | Shapeton | |
| D402,028 S | 12/1998 | Grimm et al. | |
| D408,018 S | 4/1999 | McNaughton | |
| D416,089 S | 11/1999 | Barton et al. | |
| 6,050,996 A | 4/2000 | Schmaltz et al. | |
| D424,694 S | 5/2000 | Tetzlaff et al. | |
| D425,201 S | 5/2000 | Tetzlaff et al. | |
| H1904 H | 10/2000 | Yates et al. | |
| 6,293,954 B1 | 9/2001 | Fogarty et al. | |
| D449,886 S | 10/2001 | Tetzlaff et al. | |
| 6,329,778 B1 | 12/2001 | Culp et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,406,485 B1 | 6/2002 | Hossain et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| 6,511,480 B1 | 1/2003 | Tetzlaff et al. | |
| 6,673,092 B1 | 1/2004 | Bacher | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,118,570 B2 | 10/2006 | Tetzlaff et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,329,257 B2 | 2/2008 | Kanehira et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swayer et al. | |
| 7,641,653 B2 | 1/2010 | Dalla Betta et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 9,028,492 B2 | 5/2015 | Kerr et al. | |
| 2003/0018332 A1 | 1/2003 | Schmaltz et al. | |
| 2003/0109875 A1* | 6/2003 | Tetzlaff | A61B 18/1445 606/48 |
| 2003/0229344 A1 | 12/2003 | Dycus et al. | |
| 2005/0070889 A1* | 3/2005 | Nobis | A61B 17/320016 606/45 |
| 2005/0113826 A1 | 5/2005 | Johnson et al. | |
| 2005/0113828 A1 | 5/2005 | Shields et al. | |
| 2005/0119655 A1* | 6/2005 | Moses | A61B 18/1442 606/51 |
| 2006/0253126 A1 | 11/2006 | Bjerken et al. | |
| 2007/0062017 A1 | 3/2007 | Dycus et al. | |
| 2007/0179499 A1 | 8/2007 | Garrison | |
| 2007/0260241 A1 | 11/2007 | Dalla Betta et al. | |
| 2007/0260242 A1* | 11/2007 | Dycus | A61B 18/1445 606/51 |
| 2009/0131934 A1 | 5/2009 | Odom et al. | |
| 2010/0016857 A1 | 1/2010 | McKenna et al. | |
| 2010/0063528 A1* | 3/2010 | Beaupre | A61B 17/2909 606/169 |
| 2010/0179545 A1* | 7/2010 | Twomey | A61B 18/1445 606/51 |
| 2010/0228250 A1 | 9/2010 | Brogna | |
| 2010/0292691 A1 | 11/2010 | Brogna | |
| 2010/0305567 A1 | 12/2010 | Swanson | |
| 2011/0060314 A1 | 3/2011 | Wallace et al. | |
| 2011/0072638 A1 | 3/2011 | Brandt et al. | |
| 2012/0172873 A1* | 7/2012 | Artale | A61B 18/1442 606/46 |
| 2013/0018372 A1 | 1/2013 | Sims et al. | |
| 2013/0030432 A1 | 1/2013 | Garrison et al. | |
| 2013/0041370 A1 | 2/2013 | Unger | |
| 2013/0046295 A1 | 2/2013 | Kerr et al. | |
| 2016/0157925 A1 | 6/2016 | Artale et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 2353535 A1 | 8/2011 |
| JP | 61501068 | 9/1984 |
| JP | 10-24051 A | 1/1989 |
| JP | 11-47150 A | 6/1989 |
| JP | 65502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |

(56) References Cited

FOREIGN PATENT DOCUMENTS

| | | | |
|---|---|---|---|
| JP | 07265328 | A | 10/1995 |
| JP | 8-56955 | | 3/1996 |
| JP | 08252263 | A | 10/1996 |
| JP | 8-317934 | A | 12/1996 |
| JP | 9-10223 | | 1/1997 |
| JP | 9-122138 | A | 5/1997 |
| JP | 10-155798 | A | 6/1998 |
| JP | 11-070124 | A | 3/1999 |
| JP | 11-169381 | A | 6/1999 |
| JP | 11-192238 | A | 7/1999 |
| JP | 11244298 | A | 9/1999 |
| JP | 2000-102545 | A | 4/2000 |
| JP | 2000342599 | A | 12/2000 |
| JP | 2000350732 | A | 12/2000 |
| JP | 2001-8944 | | 1/2001 |
| JP | 2001029356 | A | 2/2001 |
| JP | 2001128990 | A | 5/2001 |
| JP | 2001-190564 | A | 7/2001 |
| JP | 2004-517668 | A | 6/2004 |
| JP | 2004-528869 | A | 9/2004 |
| SU | 401367 | A1 | 10/1973 |
| WO | 94/00059 | | 1/1994 |
| WO | 99-23933 | A2 | 5/1999 |
| WO | 00/24330 | | 5/2000 |
| WO | 0036986 | A1 | 6/2000 |
| WO | 0115614 | A1 | 3/2001 |
| WO | 0154604 | A1 | 8/2001 |
| WO | 02/080793 | | 10/2002 |
| WO | 02/080793 | A1 | 10/2002 |
| WO | 02080786 | A1 | 10/2002 |
| WO | 2005/110264 | A2 | 11/2005 |

OTHER PUBLICATIONS

U.S. Appl. No. 09/177,950, filed Oct. 23, 1998, Randel a. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Homer.
U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Homer.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
Chinese Office Action and Search Report (with English translation), dated Feb. 27, 2017, corresponding to Chinese Application No. 201410385013.5; 17 total pages.
European Search Report dated Mar. 20, 2017, corresponding to European Application No. 13891030.2; 7 pages.
"Electrosurgery: A Historical Overview" Innovations in Electrosurgery; Sales/Product Literature; Dec. 31, 2000.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work, quadrature.Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrell et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
International Search Report and Written Opinion of the International Searching Authority dated Jan. 17, 2013 from counterpart International Application No. PCT/US2012/050094 (8 pgs.).
European Search Report, dated Feb. 19, 2015, corresponding to European Patent Application No. 12824142.9; 6 pages.
European Extended Search Report dated Jun. 29, 2015, corresponding to European Application No. 12824142.9; 10 pages.
English translation of first Chinese Office Action and Search Report dated Aug. 28, 2015, corresponding to Chinese Patent Application No. 201280035427.4; 9 total pages.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" Innovations That Work, quadrature 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
Australian Examination Report issued in Appl. No. AU 2013397838 dated Apr. 20, 2018 (3 pages).
European Examination Report pursuant to Article 94(3) EPC issued in corresponding Appl. No. EP 13891030.2 dated Oct. 24, 2019 (5 pages).

* cited by examiner

BIPOLAR SURGICAL INSTRUMENT WITH TISSUE STOP

CROSS REFERENCE TO RELATED APPLICATION

The present application is a U.S. National Stage Application under 35 U.S.C. § 371(a) of PCT/CN2013/080954 filed Aug. 7, 2013, the entire contents of which are incorporated by reference herein.

BACKGROUND

1. Background of Related Art

The present disclosure relates to forceps used for open surgical procedures. More particularly, the present disclosure relates to a bipolar forceps for treating tissue that is capable of sealing and cutting tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

SUMMARY

The present disclosure relates to forceps used for open surgical procedures. More particularly, the present disclosure relates to a bipolar forceps for treating tissue that is capable of sealing and cutting tissue.

As is traditional, the term "distal" refers herein to an end of the apparatus that is farther from an operator, and the term "proximal" refers herein to the end of the bipolar forceps that is closer to the operator.

The bipolar forceps includes a mechanical forceps including first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. A disposable housing is configured to releasably couple to one or both shafts. An electrode assembly has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue to effect a tissue seal. One or both of the electrodes includes a knife channel defined along its length. The knife channel is configured to receive a knife blade therethrough to cut tissue grasped between the jaw members. A tissue stop disposed between at least a portion of the distal ends of the shafts is configured to prevent tissue held between the electrodes from moving proximal to the tissue stop. A knife slot is defined through the tissue stop and is configured to align with the knife channel to receive the knife blade. An actuation mechanism is at least partially disposed within the housing and is configured to selectively advance the knife blade through the knife channel to cut tissue.

Additionally or alternatively, the tissue stop may be constructed from a flexible material.

Additionally or alternatively, the tissue stop may be configured to expand and contract upon movement of the jaw members between the first and second positions.

Additionally or alternatively, the pivot may define a longitudinal slot therethrough and the knife blade may be configured to move within the longitudinal slot.

Additionally or alternatively, the longitudinal slot may be configured to longitudinally align with the knife slot defined through the tissue stop when the jaw members are in the second position.

Additionally or alternatively, the bipolar forceps may also include a knife guide supported in the housing. A longitudinal slot may be defined through the knife guide that receives the knife blade therein.

Additionally or alternatively, the longitudinal knife slot defined through the knife guide may be configured to longitudinally align with the knife slot defined through the tissue stop when the jaw members are in the second position.

Additionally or alternatively, the bipolar forceps may also include a knife lockout mechanism configured to prohibit advancement of the knife blade into the knife channel when the jaw members are in the first position.

According to another aspect of the present disclosure, a bipolar forceps is provided. The bipolar forceps includes a mechanical forceps including first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. A disposable housing is configured to releasably couple to one or both shafts. An electrode assembly has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue held between the electrodes to effect a tissue seal. One or both of the electrodes includes a knife channel defined along its length. The knife channel is configured to receive a knife blade therethrough to cut tissue grasped between the jaw members. A flexible tissue stop is disposed between at least a portion of the distal ends of the shafts configured to prevent tissue held between the electrodes from moving proximal to the tissue stop. The tissue stop is configured to expand and contract upon movement of the jaw members between the first and second positions. A knife slot is defined through the tissue stop and is configured to align with the knife channel to receive the knife blade therethrough. A knife guide is supported in the housing and has a longitudinal slot defined therethrough configured to longitudinally align with the knife slot defined through the tissue stop when the jaw members are in the second position to permit advancement of the knife blade into the knife channel. An actuation mechanism is at least partially disposed within the housing and is configured to selectively advance the knife blade through the knife slots defined through the knife guide and the tissue stop and into the knife channel to cut tissue.

Additionally or alternatively, the pivot may define a longitudinal slot therethrough configured to longitudinally align with the knife slot defined through the tissue stop when the jaw members are in the second position.

Additionally or alternatively, the bipolar forceps may also include one or more handle members extending from the housing and operably coupled to the actuation mechanism. The one or more handle members are moveable relative to the housing to effect advancement of the knife blade through the knife slots defined through the knife guide and the tissue stop and into the knife channel to cut tissue.

Additionally or alternatively, each of the electrodes may include an electrically conductive sealing surface and an insulating substrate coupled to the electrically conductive sealing surface.

Additionally or alternatively, each of the electrodes may include one or more mechanical interfaces configured to complement a corresponding mechanical interface on one of the jaw members to releasably couple the electrode to the jaw member.

Additionally or alternatively, the bipolar forceps may also include a knife lockout mechanism configured to be engaged by one or both shafts to move the knife lockout mechanism from a first position wherein the knife lockout mechanism engages the actuation mechanism to prohibit advancement of the knife blade into the knife channel when the jaw members are in the first position to a second position wherein the knife lockout mechanism disengages the actuation mechanism when the jaw members are in the second position to permit advancement of the knife blade through the knife channel.

BRIEF DESCRIPTION OF THE DRAWINGS

Various embodiments of the subject instrument are described herein with reference to the drawings wherein.

DETAILED DESCRIPTION

Figure 1:
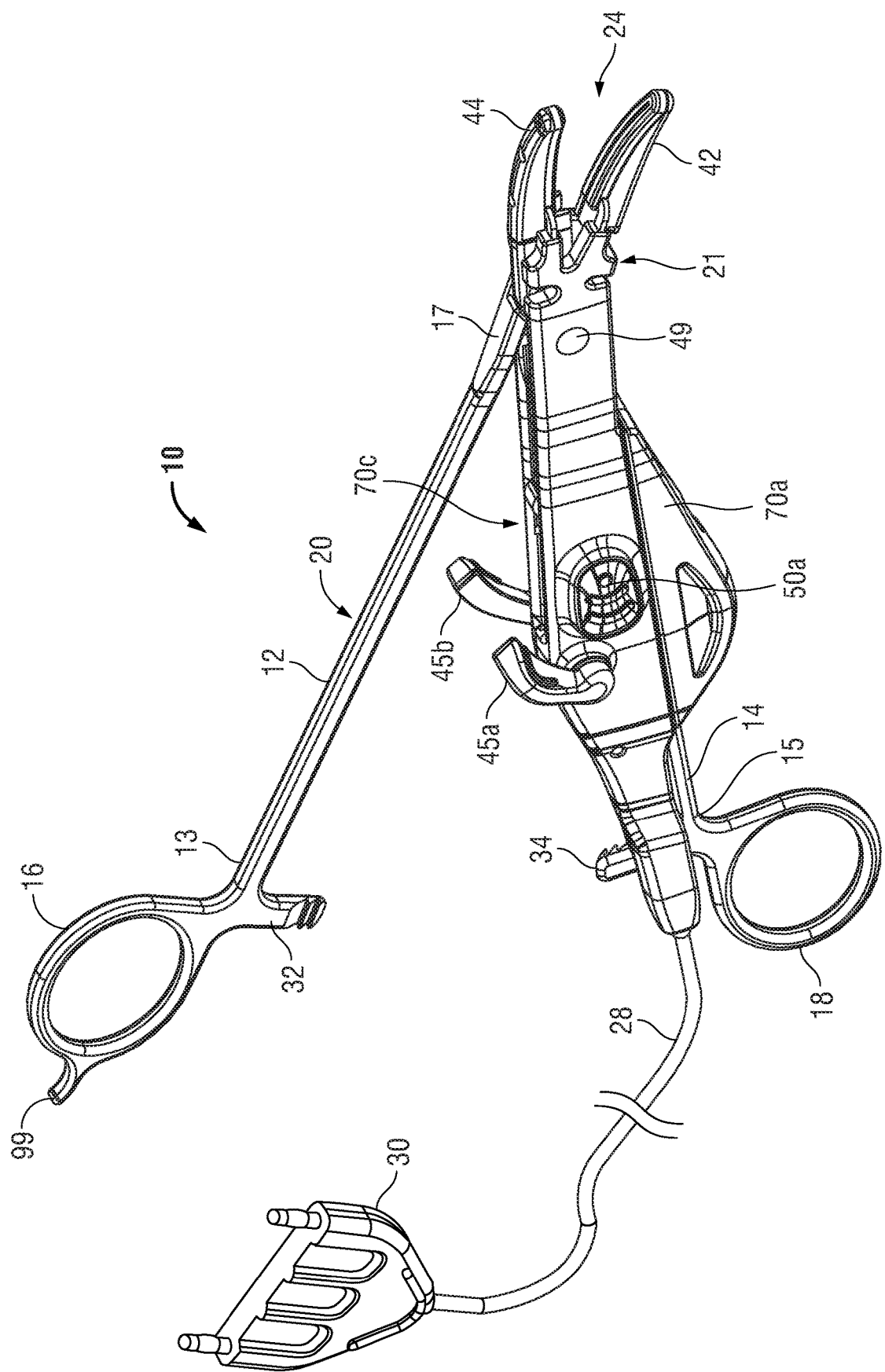
FIG. 1 is a perspective view of a bipolar forceps according to an embodiment of the present disclosure including a mechanical forceps, a disposable housing, and an electrode assembly.
Figure 2A:
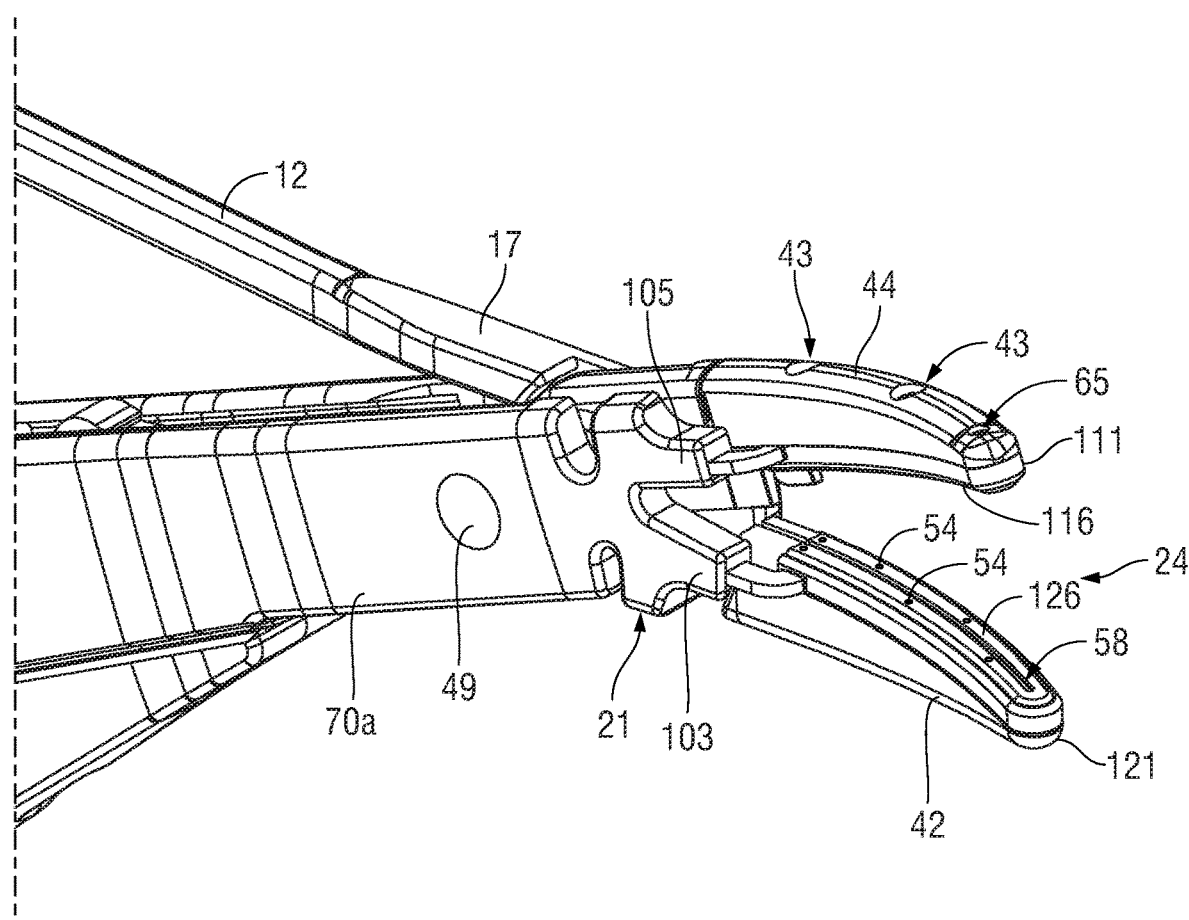
FIG. 2A is an enlarged, perspective view of a distal end of the bipolar forceps of FIG. 1.
Figure 2B:
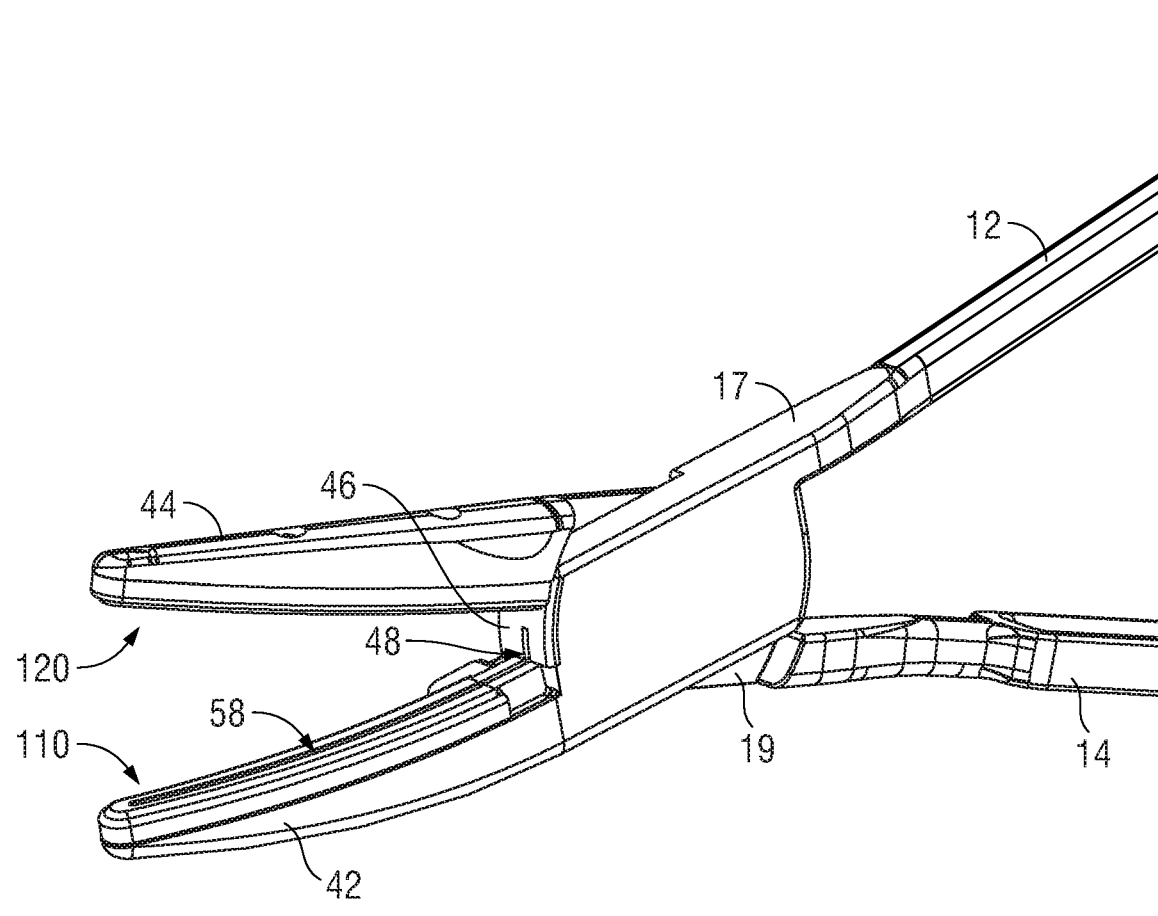
FIG. 2B is an enlarged, perspective view of a distal end of the bipolar forceps of FIG. 1 with parts partially removed.
Figure 3:
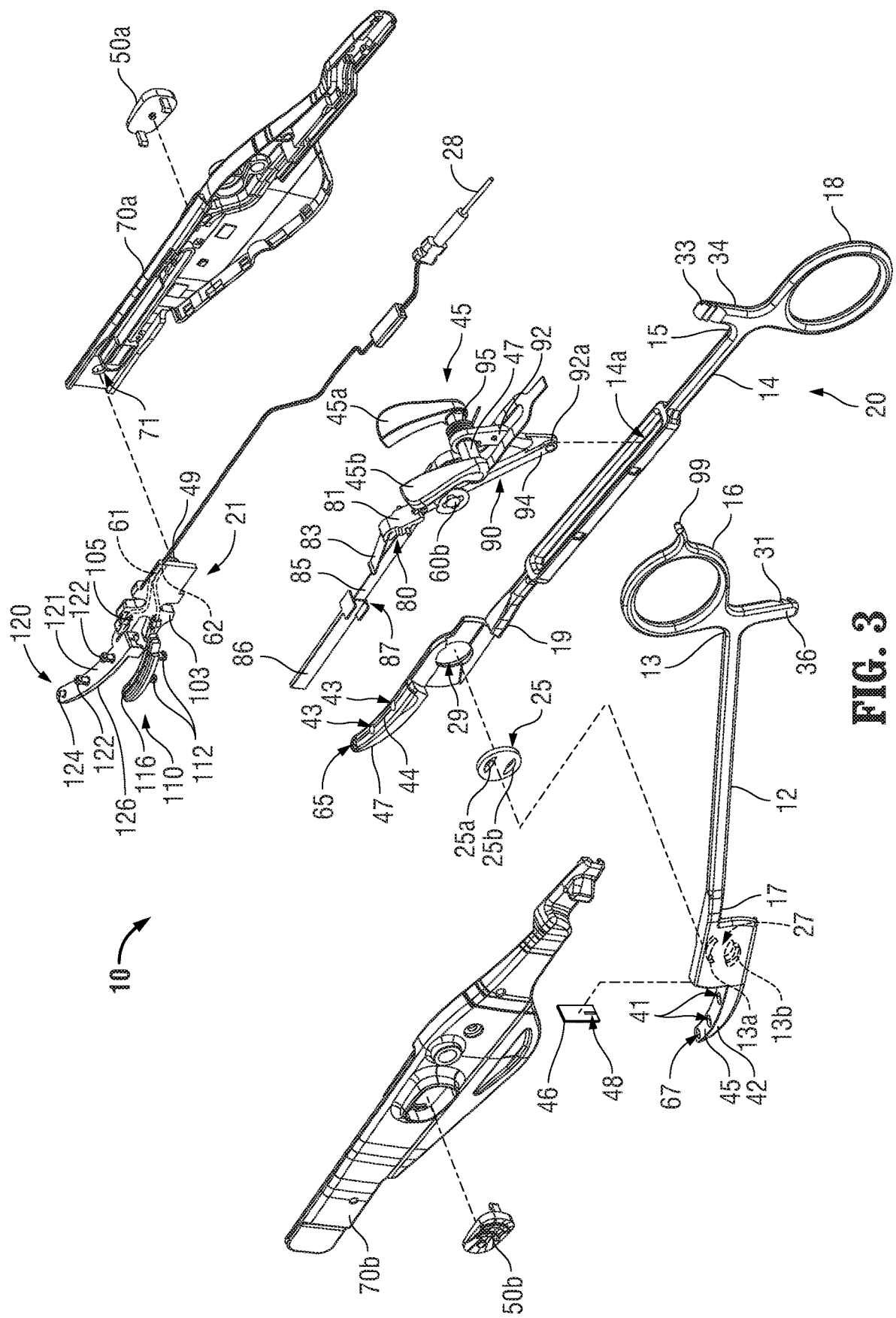
FIG. 3 is a perspective view of the bipolar forceps of FIG. 1 with parts separated.

Referring initially to FIGS. 1-3, a bipolar forceps 10 for use with open surgical procedures includes a mechanical forceps 20 having an end effector 24 and a disposable electrode assembly 21. Mechanical forceps 20 includes first and second elongated shaft members 12 and 14. Elongated shaft member 12 includes proximal and distal end portions 13 and 17, respectively, and elongated shaft member 14 includes proximal and distal end portions 15 and 19, respectively. Disposed at proximal end portions 13, 15 of shaft members 12, 14 are handle members 16 and 18, respectively, that are configured to allow a user to effect movement of at least one of the shaft members 12 and 14 relative to the other. The end effector 24 includes opposing jaw members 42, 44 that extend from the distal end portions 17 and 19 of shaft members 12 and 14, respectively. The jaw members 42, 44 are movable relative to each other in response to movement of shaft members 12, 14.

Figure 8:
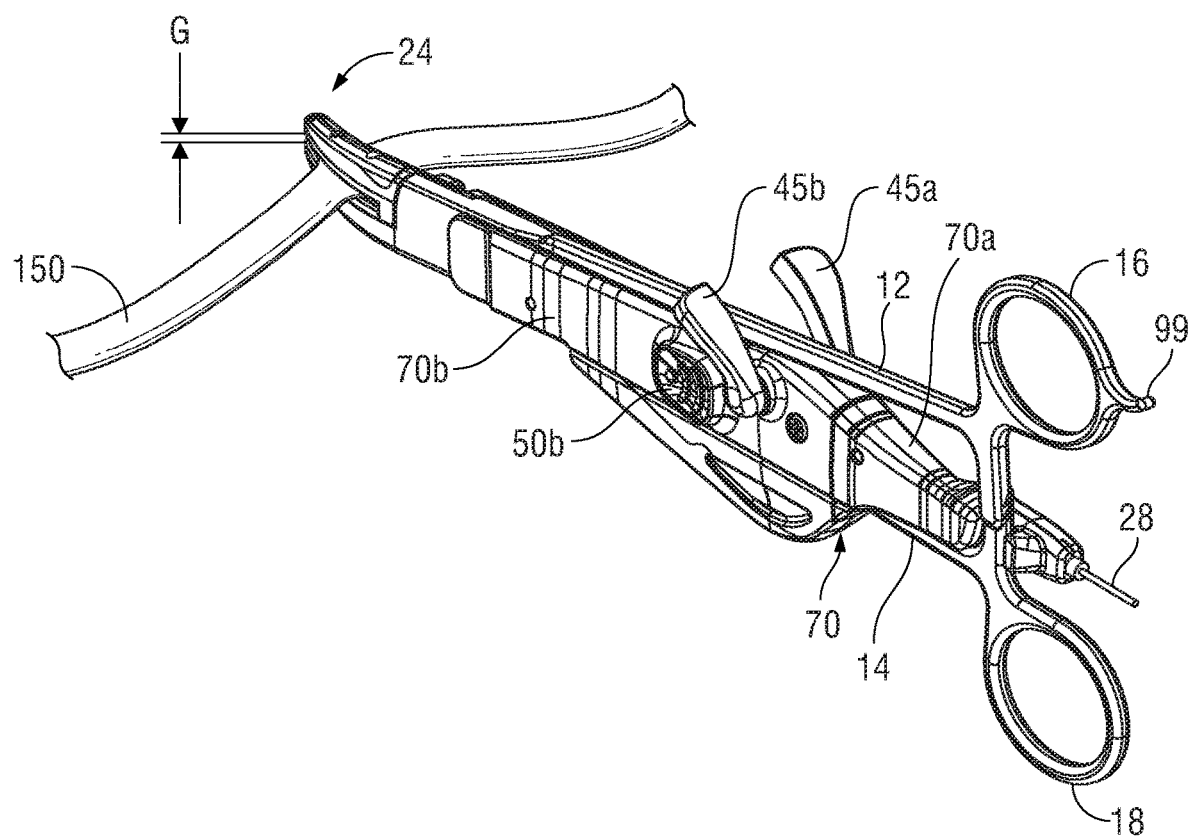
FIG. 8 is a perspective view of the bipolar forceps of FIG. 1 grasping tissue to effect a tissue seal.

Shaft members 12 and 14 are affixed to one another at their distal end portions 17 and 19, respectively, by a pivot 25 such that movement of shaft members 12, 14, imparts movement of the jaw members 42, 44 from an open position or configuration (FIG. 9A) wherein the jaw members 44, 42 are disposed in spaced relation relative to one another to a closed position or configuration (FIGS. 9B and 9C) wherein the jaw members 42, 44 cooperate to clamp or grasp tissue 150 therebetween (FIG. 8). In some embodiments, the forceps 10 may be configured such that movement of one or both of the shaft members 12, 14 causes only one of the jaw members to move with respect to the other jaw member. Pivot 25 includes a pair of generally semi-circular shaped apertures 25a, 25b disposed therethrough and is configured to be seated in a pivot aperture 29 (FIG. 3) such that pivot 25 is permitted to freely rotate within pivot aperture 29, as further detailed below.

Each shaft member 12 and 14 also includes a ratchet portion 32 and 34, respectively. Each ratchet 32, 34 extends from the proximal end portion 13, 15 of its respective shaft member 12, 14 towards the other ratchet in a generally vertically aligned manner such that the inner facing surfaces of each ratchet 32 and 34 abut one another when the shaft members 12, 14 are approximated. Each ratchet 32 and 34 includes a plurality of flanges 31 and 33 (FIG. 3), respectively, that project from the inner facing surface of each ratchet 32 and 34 such that the ratchets 32 and 34 may interlock at one or more positions. In some embodiments, each ratchet position holds a particular strain energy in the shaft members 12 and 14 to impart a specific closure force to the end effector 24. At least one of the shaft members, e.g., shaft member 12, includes a tang 99 that facilitates manipulation of forceps 20 during surgical conditions as well as facilitates attachment of electrode assembly 21 on mechanical forceps 20 as will be described in greater detail below.

Referring to FIGS. 2A and 3, disposable electrode assembly 21 is configured to releasably couple to mechanical forceps 20, as detailed below, and is operably coupled to a housing 70 having a pair of housing halves 70a, 70b configured to matingly engage and releasably encompass at least a portion of shaft member 14. Housing 70 also serves to house a knife 85 having a sharpened distal cutting edge 89 (FIG. 9C), a knife guide 86 having a longitudinal slot 87 (FIG. 3) configured to receive the knife blade 85 therein, and a knife actuation mechanism 90 configured to effect advancement of the knife blade 85 through a knife channel 58 (FIG. 2A) defined in one or both electrodes 110, 120 to transect tissue, as further detailed below. An interior of each of housing half 70a, 70b may include a plurality of cooperating mechanical interfaces disposed at various positions to effect mechanical coupling of housing halves 70a, 70b to form housing 70.

As shown in FIGS. 2B and 3, a tissue stop 46 is disposed at distal ends 17 and 19 of shaft members 12 and 14, respectively, and distal to pivot 25. Tissue stop 46 includes a knife slot 48 defined therethrough configured to align with knife channel 58 such that knife blade 85 moves through knife slot 48 upon entering and exiting knife channel 58. In some embodiments, tissue stop 46 is constructed from a flexible biocompatible material such as, for example, an injection molded polymer, that allows tissue stop 46 to expand and contract upon movement of jaw members 42, 44 between the open (FIG. 9A) and closed (FIG. 9B) configurations to maintain a coupling with distal ends 17, 19 of shaft members 12, 14, respectively. As detailed further below, upon assembly of mechanical forceps 20, a space or passageway may be defined between the distal ends 17 and 19 of shaft members 12 and 14, respectively, to allow for the passage of the knife blade 85 therethrough. The tissue stop 46 serves to prevent tissue grasped between jaw members 42, 44 from moving proximally of the tissue stop 46 or from entering the space or passageway defined between the distal ends 17 and 19 of shaft members 12 and 14, respectively, without impeding movement of knife blade 85 into and out of knife channel 58. In some embodiments, tissue stop 46 may be at least partially disposed between the distal ends 17 and 19 of shaft members 12 and 14, respectively.

Figure 4:
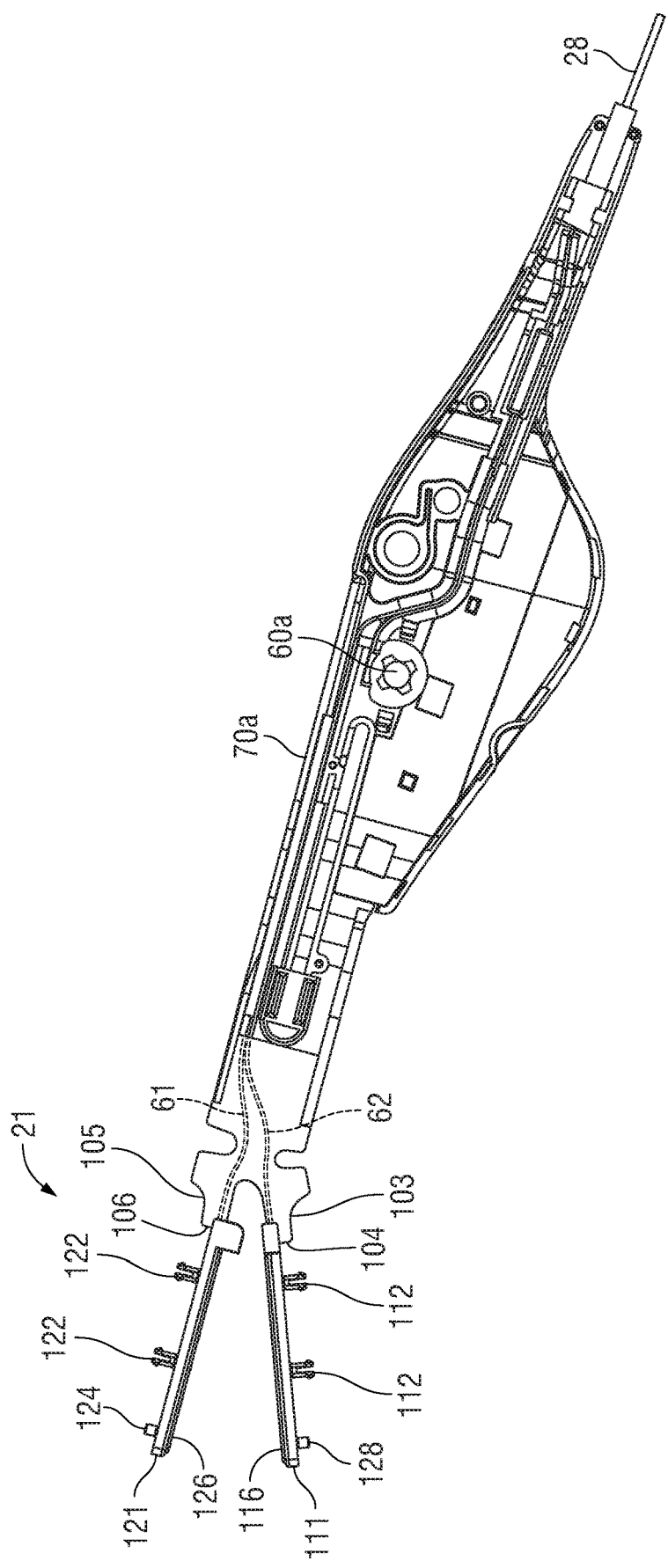
FIG. 4 is an enlarged, side view of the disposable housing and the electrode assembly of FIG. 1 with parts partially removed.
Figure 6:
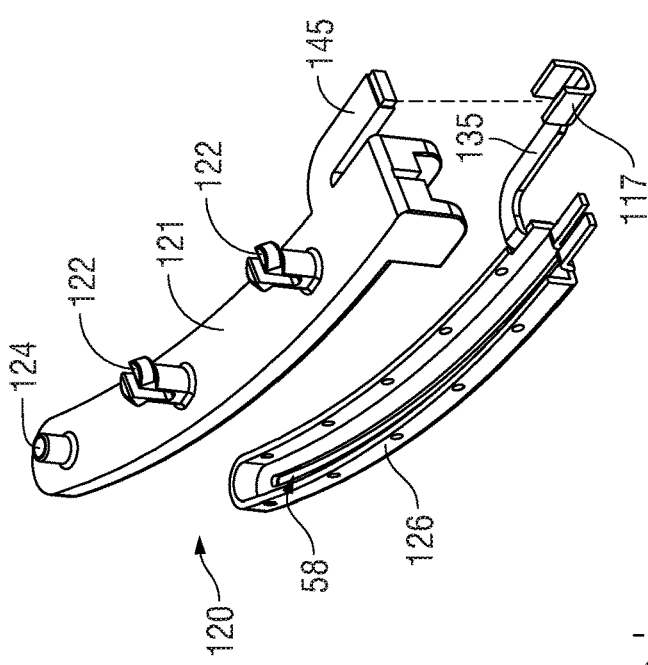
FIGS. 6 and 7 are perspective views of electrodes of the electrode assembly of FIG. 1 with parts separated.
Figure 5:
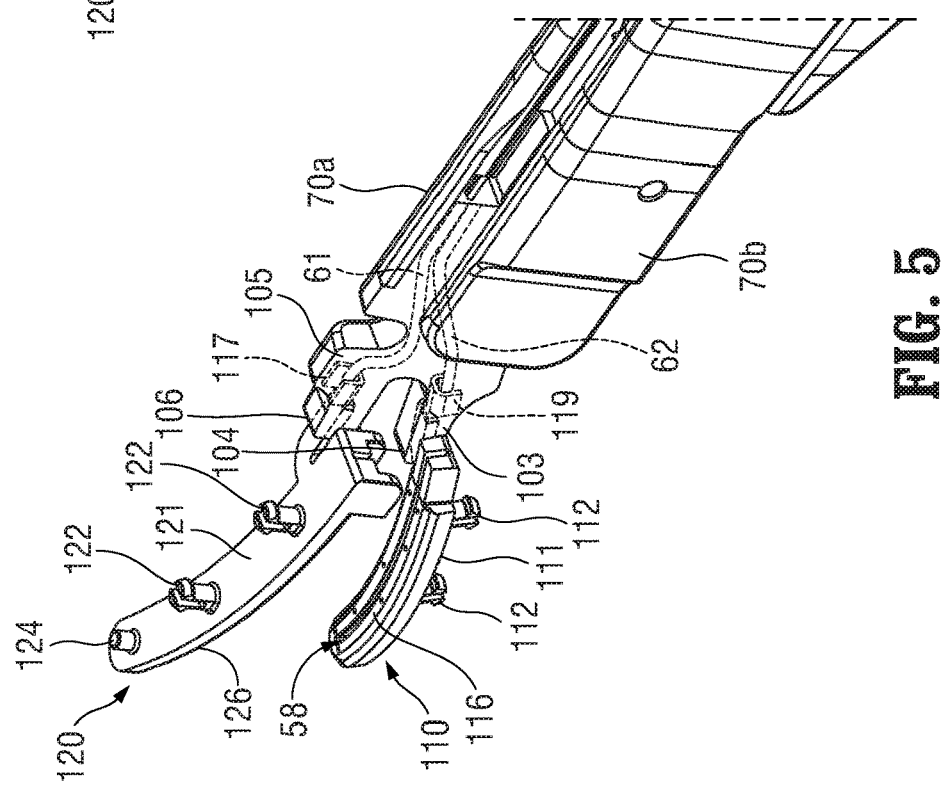
FIG. 5 is an enlarged, perspective view of the electrode assembly of FIG. 1.

As shown in FIGS. 4 and 5, a pair of wires 61 and 62 are electrically connected to the electrodes 120 and 110, respectively, and are bundled to form a cable 28 that extends through housing 70 and terminates at a terminal connector 30 (FIGS. 1 and 3) configured to mechanically and electrically couple to a suitable energy source such as an electrosurgical generator (not shown). One example of an electrosurgical generator is the LIGASURE® Vessel Sealing Generator and the ForceTriad® Generator sold by Covidien. In some embodiments, one or both of handle members 16 and 18 may include a suitable mechanical interface (e.g., a wire holder) configured to releasably retain cable 28 to aid in keeping cable 28 from interfering with a surgeon's hands during operation of forceps 10.

Referring now to FIGS. 3-7, electrode assembly 21 includes a generally circular boss member 49 configured to be seated (e.g., in a friction fit manner) within a complementary aperture 71 disposed through a distal end of housing half 70a to releasably attach electrode assembly 21 thereto. Electrode assembly 21 is bifurcated such that two prong-like members 103 and 105 extend distally therefrom to support electrodes 110 and 120, respectively. Electrode 120 includes an electrically conductive sealing surface 126 configured to conduct electrosurgical energy therethrough and an electrically insulative substrate 121 that serves to electrically insulate jaw member 42 from sealing surface 126. Sealing surface 126 and substrate 121 are attached to one another by any suitable method of assembly such as, for example, snap-fit engagement or by overmolding substrate 121 to sealing surface 126. In some embodiments, substrate 121 is made from an injection molded plastic material. Substrate 121 includes a plurality of bifurcated anchor members 122 extending therefrom that are configured to compress during insertion into a corresponding plurality of sockets 41 disposed at least partially through an inner facing surface 45 (FIG. 3) of jaw member 42 and subsequently expand to releasably engage corresponding sockets 41 after insertion to couple electrode 120 to inner facing surface 45. Substrate 121 also includes an alignment pin 124 (FIG. 6) that is configured to engage an aperture 67 disposed at least partially through inner facing surface 45 of jaw member 42 to ensure proper alignment of electrode 120 with jaw member 42 during assembly. Conductive sealing surface 126 includes an extension 145 having a wire crimp 117 configured to be inserted into the distal end 106 of prong 105 of electrode assembly 21 and electrically connect to wire 61 disposed therein (FIG. 5).

Figure 7:
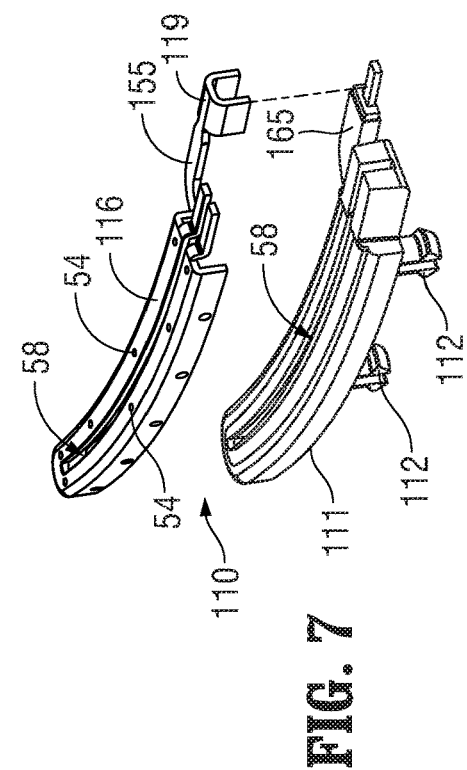

Substantially as described above with respect to electrode 120, electrode 110 includes an electrically conductive sealing surface 116 configured to conduct electrosurgical energy therethrough and an electrically insulative substrate 111 attached thereto, as shown in FIG. 7. Substrate 111 includes a plurality of bifurcated anchor members 112 extending therefrom that are configured to compress during insertion into a corresponding plurality of sockets 43 disposed at least partially through an inner facing surface 47 (FIG. 3) of jaw member 44 and subsequently expand to releasably engage corresponding sockets 43 after insertion to couple electrode 110 to inner facing surface 47. Substrate 111 also includes an alignment pin 128 (FIG. 4) that is configured to engage an aperture 65 disposed at least partially through inner facing surface 47 of jaw member 44 to ensure proper alignment of electrode 110 with jaw member 44 during assembly. Sealing surface 116 includes an extension 155 having a wire crimp 119 extending therefrom configured to be inserted into the distal end 104 of prong 103 of electrode assembly 21 and electrically connect to wire 62 disposed therein. Substrate 111 includes an extension 165 extending proximally therefrom and configured to couple to extension 155 of sealing surface 116.

Referring to FIG. 4, at least one of the prong members 103, 105 is flexible such that prong members 105 and 103 are readily moveable relative to each other. In some embodiments, the electrode assembly 21 is removably attached to the mechanical forceps 20 by initially moving prongs 103, 105 towards each other. While jaw members 42, 44 are in an open configuration, the electrodes 120 and 110 may be slid between opposing jaw members 42 and 44 such that anchor members 122 and 112 and guide pins 128 and 124, respectively, may be aligned with and releasably inserted into corresponding sockets 41 and 43 or apertures 67 and 65, respectively, to couple electrodes 120 and 110 with jaw member 42 and 44, respectively. Housing halves 70a, 70b may then be releasably coupled to form housing 70 to encompass at least a portion of shaft member 14 in the manner described above.

To electrically control the end effector 24, the housing 70 supports a pair of depressible activation buttons 50a, 50b that are operable by the user to actuate corresponding switches 60a, 60b, respectively, disposed within housing 70. Switches 60a, 60b are electrically interconnected with wires 61, 62, respectively, and serve to initiate and terminate the delivery of electrosurgical energy from a suitable energy source to the end effector 24 to effect a tissue seal.

Once a tissue seal is established, the knife blade 85 may be advanced through the knife channel 58 to transect the sealed tissue, as detailed below. However, in some embodiments, knife blade 85 may be advanced through the knife channel 58 before, during, or after tissue sealing. In some embodiments, a knife lockout mechanism 80 is provided to prevent extension of the knife blade 85 into the knife channel 58 when the jaw members 42, 44 are in the open configuration, thus preventing accidental or premature transection of tissue, as detailed below.

Figure 9A:
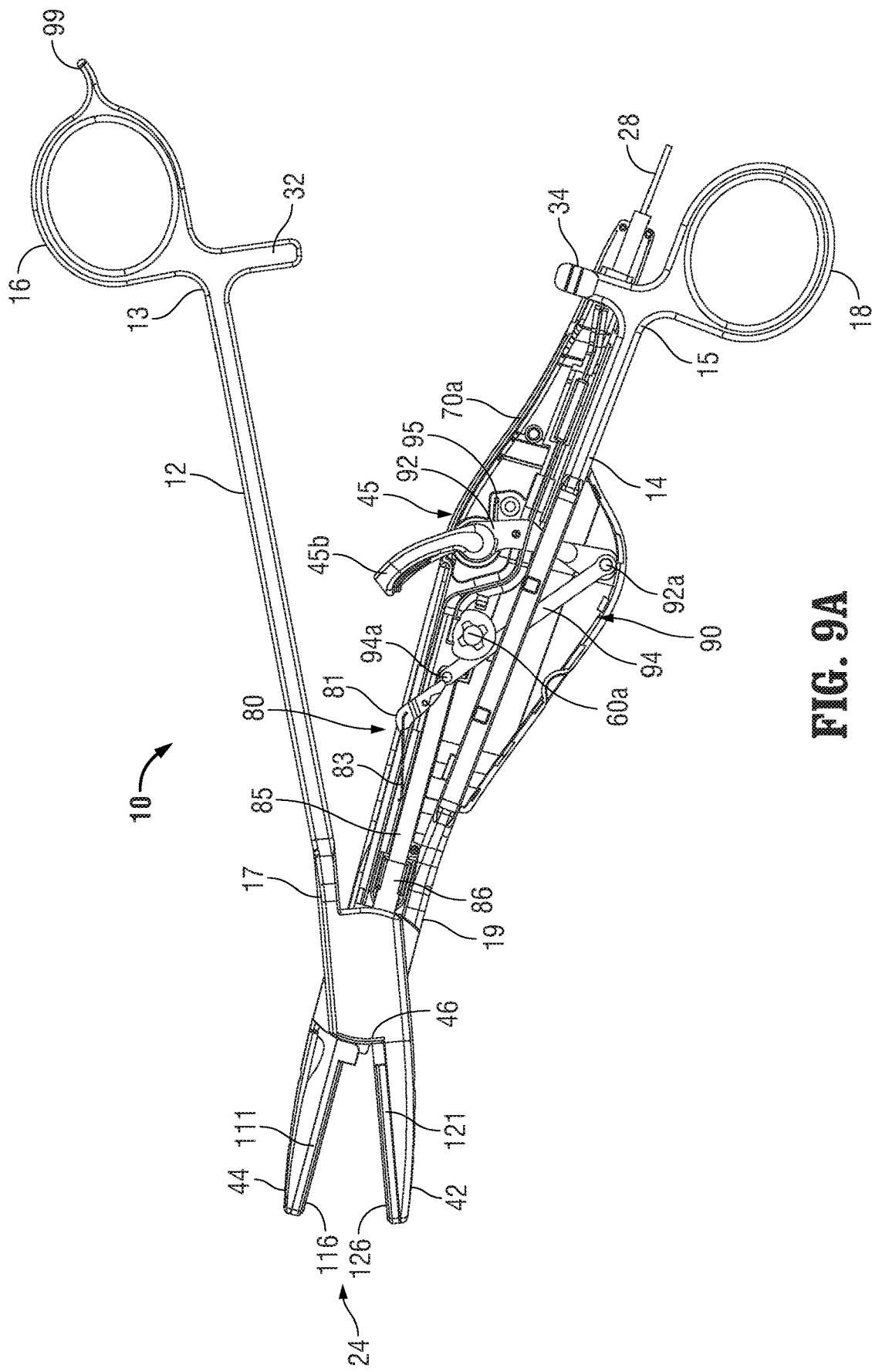
FIGS. 9A-9C are side views of the bipolar forceps of FIG. 1 depicting a sequence of motions to illustrate operation of the bipolar forceps.

With reference to FIG. 3, the knife actuation mechanism 90 is operably associated with a trigger 45 having opposing handle members 45a, 45b extending from opposing sides of housing 70. Upon actuation of handle members 45a, 45b, the knife actuation mechanism 90 responds utilizing a series of inter-cooperating elements to actuate the knife blade 85 through knife slot 48 and subsequently through knife channel 58 to sever tissue grasped between jaw members 42, 44, as detailed below with reference to FIG. 9C. More specifically, the knife actuation mechanism 90 includes a first link 92 operably coupled at one end to a shaft member 47 and at an opposing end to a second link 94 by a pivot pin 92a. Shaft member 47 extends laterally through housing 70 to operably connect handle members 45a, 45b from opposing sides of housing 70. The second link 94 is operably coupled at one end to the first link 92 by the pivot pin 92a and at the other end to a proximal end of the knife blade 85 by a pivot pin 94a (FIG. 9A). Shaft member 14 defines a longitudinal slot 14a therethrough that is configured to receive first and second links 92, 94 therein. First and second links 92, 94 extend through longitudinal slot 14a and are free to move therethrough upon actuation of the handle members 45a, 45b, as further detailed below with reference to FIG. 9C.

Figure 9B:
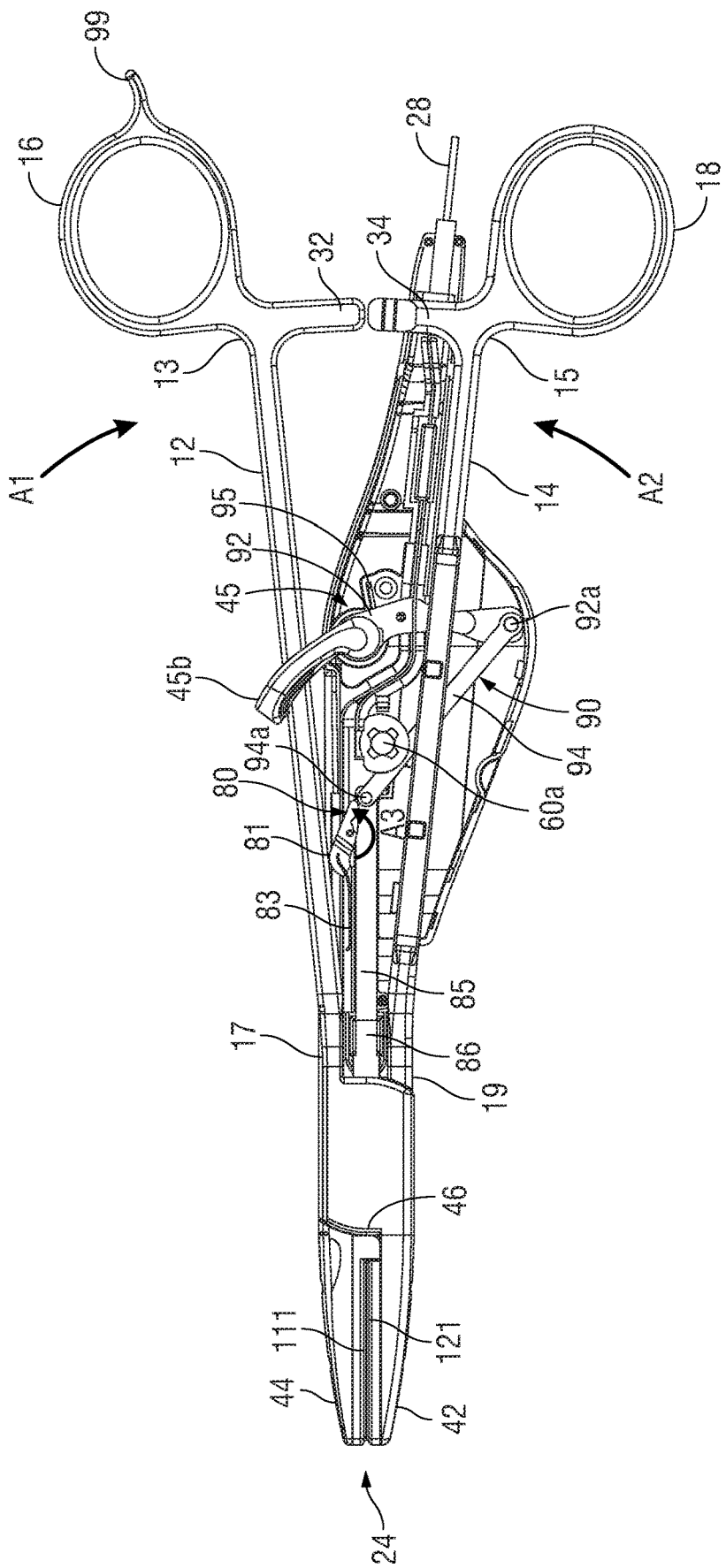

A biasing member 95 (e.g., torsion spring) is disposed coaxially about at least a portion of the shaft member 47 between the first link 92 and handle member 45a. The biasing member 95 is operably coupled at one end to a portion of the first link 92 and at the other end to a suitable mechanical interface within the housing 70 that braces or stabilizes biasing member 95 during use of the knife actuation mechanism 90. The biasing member 95 serves to bias the trigger 45 such that subsequent to actuation of the knife blade 85 through the knife channel 58 (FIG. 9C), handle members 45a, 45 are biased to return to an unactuated position (FIGS. 9A and 9B), thereby retracting the knife blade 85 proximally to an unactuated position (FIGS. 9A and 9B).

With reference to FIG. 3, pivot 25 includes a pair of apertures 25a, 25b disposed therethrough that are configured to receive a pair of complementary raised portions 13a, 13b therein, respectively, extending from the distal end portion 17 of shaft member 12 and defining a longitudinal passageway 27 therebetween. Upon movement of jaw members 42, 44 to the closed configuration (FIG. 9B), longitudinal passageway 27 is longitudinally aligned with knife slot 48 and knife channel 58. Raised portions 13a, 13b extend sufficiently from the distal portion of shaft member 14 so that apertures 25a, 25b may receive raised portions 13a, 13b therein, respectively, while maintaining pivot 25 in spaced relation with the distal portion of shaft member 14 to allow the knife guide 86 to be received through passageway 27 and into alignment with knife slot 48 of tissue stop 46 when jaw members 42, 44 are in the closed configuration (FIG. 9B). Tissue is prevented from entering passageway 27 by tissue stop 46. Movement of shaft members 12, 14 relative to each other causes rotational movement of pivot 25 within pivot aperture 29.

A knife guide 86 is supported within the housing 70 between the end effector 24 and the knife actuation mechanism 90 and extends through passageway 27. The knife guide 86 includes a longitudinal slot 87 that provides lateral support to the knife blade 85 and constrains side-to-side lateral motion of the knife blade 85. Thus, the knife guide 86 serves to urge the knife blade 85 into a central position relative to end effector 24, thereby ensuring proper alignment of the knife blade 85 as the knife blade 85 advances through knife slot 48 defined through tissue stop 46 and enters the knife channel 58 defined in electrodes 110, 120.

Figure 9C:
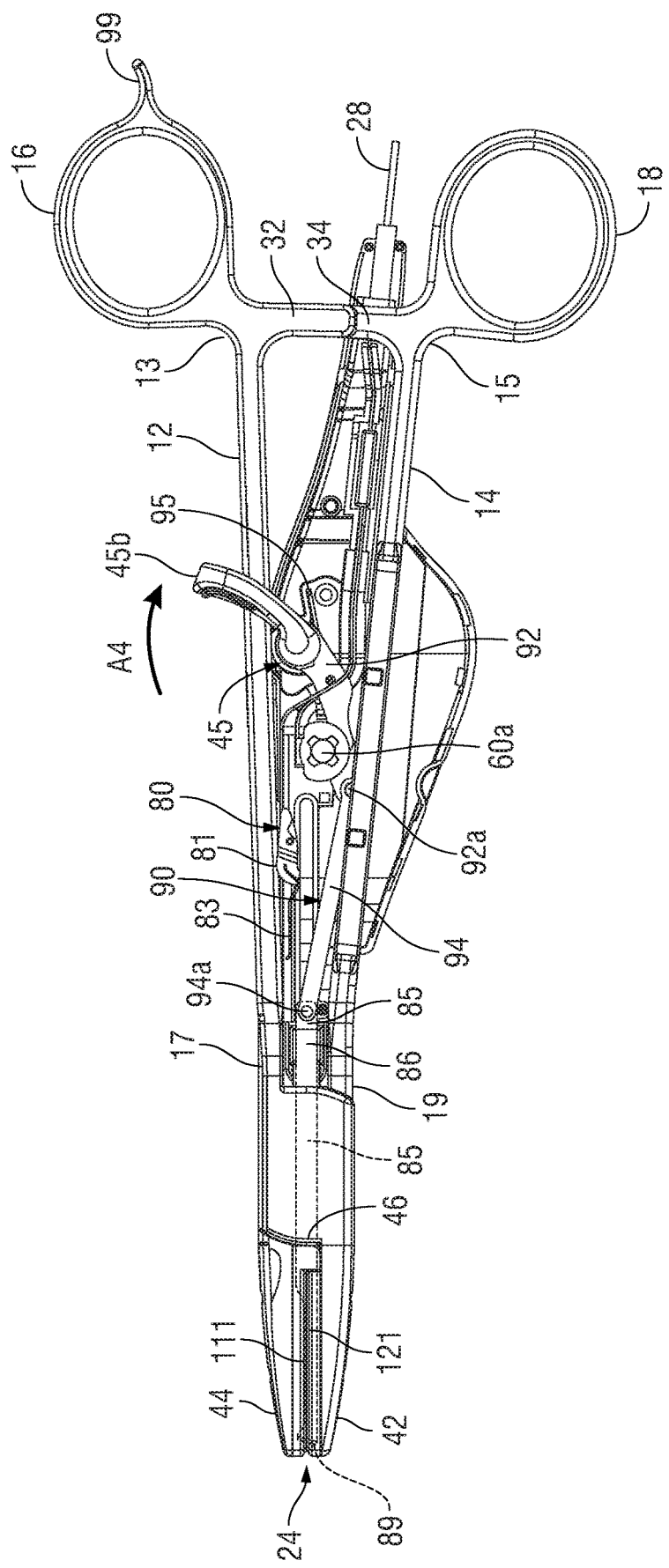

In some embodiments, the forceps 10 includes a knife blade lockout mechanism 80 supported within the housing 70 and that serves to prevent advancement of the knife blade 85 into the knife channel 85 when the jaw members 42, 44 are in the open configuration (FIG. 9A). With reference to FIG. 3, the knife blade lockout mechanism 80 includes a safety link 81 operably coupled with a biasing member 83 (e.g., a leaf spring) and pivotally supported within the housing 70. In the open configuration of jaw members 42, 44, the knife blade 85 is in an unactuated position (FIGS. 9A and 9B) and the safety link 81 is engaged with pivot pin 94a (FIG. 9A) such that distal advancement of knife blade 85 is prohibited. As shown in FIG. 1, housing 70 includes a longitudinal opening 70c that opposes shaft member 12 and exposes the knife blade lockout mechanism 80 such that upon approximation of the shaft members 12, 14 to move the jaw members 42, 44 to the closed configuration (FIG. 9B), safety link 81 is engaged by shaft member 12. Pressure applied to safety link 81 by approximation of shaft members 12, 14 operates to bias the biasing member 83 against the knife blade 85 and, in turn, rotate the safety link 81 out of engagement with the pivot pin 94a (FIG. 9B) such that knife blade 85 is permitted to advance distally into the knife channel 58 (FIG. 9C). Operation of the knife actuation mechanism 90, the knife lockout mechanism 80, and actuation of the knife blade 85 is further detailed below with reference to FIGS. 9A-9C.

The tissue seal thickness and tissue seal effectiveness may be influenced by the pressure applied to tissue between jaw members 44, 42 and the gap distance between the opposing electrodes 110 and 120 (FIG. 5) during tissue sealing. In the closed configuration, a separation or gap distance "G" may be maintained between the sealing surfaces 116, 126 by an array of stop members 54 (FIG. 2A) disposed on one or both of sealing surfaces 116, 126 (only shown disposed on sealing surface 126 for purposes of illustration). The stop members 54 contact the sealing surface on the opposing jaw member and prohibit further approximation of the sealing surfaces 116, 126. In some embodiments, to provide an effective tissue seal, an appropriate gap distance of about 0.001 inches to about 0.010 inches and, desirably, between about 0.002 and about 0.005 inches may be provided. In some embodiments, the stop members 54 are constructed of an electrically non-conductive plastic or other material molded onto the sealing surfaces 116, 126, e.g., by a process such as overmolding or injection molding. In other embodiments, the stop members 54 are constructed of a heat-resistant ceramic deposited onto sealing surfaces 116, 126.

FIG. 8 shows the bipolar forceps 10 during use wherein the shaft members 12 and 14 are approximated to apply clamping force to tissue 150 and to effect a tissue seal. Once sealed, tissue 150 may be cut along the tissue seal through actuation of the knife blade 85, as detailed below with reference to FIGS. 9A-9C.

Referring now to FIGS. 9A, 9B, and 9C, a sequence of motions may be initiated by moving the shaft members 12, 14 in order to close the jaw members 42, 44, and by rotating the handle members 45a, 45b to induce the knife actuation mechanism 90 to translate the knife blade 85 through the knife channel 58. Initially, shaft members 12, 14 are in the open configuration and the handle members 45a, 45b are in an un-actuated position as depicted in FIG. 9A. This arrangement of shaft members 12, 14 and handle members 45a, 45b sustains the end effector 24 in the open configuration wherein the jaw members 42, 44 are substantially spaced from one another, and the knife blade 85 is in a retracted or proximal position with respect to the jaw members 42, 44. The initial position of the handle members 45a, 45b depicted in FIGS. 9A and 9B is actively maintained by the influence of the biasing member 95 on the trigger 45. When jaw members 42, 44 are in the open configuration, as depicted in FIG. 9A, safety link 81 is engaged with pivot pin 94a such that rotational motion of the handle members 45a, 45b in a proximal direction (depicted by rotational arrow A4 in FIG. 9C) is prohibited so that knife blade 85 is prohibited from advancing into knife channel 58.

The jaw members 42, 44 may be moved from the open configuration of FIG. 9A to the closed configuration depicted in FIG. 9B. As the shaft members 12, 14 pivot about pivot 25 in the directions of arrows A1 and A2 (FIG. 9B), respectively, shaft member 12 engages safety link 81. As the shaft members 12, 14 pivot further about pivot 25 in the directions of arrows A1 and A2, respectively, shaft member 12 applies a force on the safety link 81 that causes biasing member 83 to flex against the bias of knife blade 85, thereby inducing rotation of the safety link 81 in the direction depicted by rotational arrow A3 in FIG. 9B. Rotation of safety link 81 in the direction of rotational arrow A3 operates to move the safety link 81 out of engagement with pivot pin 94a as shown in FIG. 9C.

Upon movement of the safety link 81 out of engagement with the pivot pin 94a, handle members 45a, 45b may be selectively moved from the unactuated configuration of FIGS. 9A and 9B to the actuated position of FIG. 9C to advance the knife blade 85 distally through knife slot 48 and into knife channel 58. More specifically, as handle members 45a, 45b rotate in the general proximal direction, depicted by rotational arrow A4, to the actuated configuration depicted in FIG. 9C, the first link 92 imparts a rotational force on second link 94, thereby causing second link 94 to rotate about pivot pin 94a and move in a general distal direction to advance knife blade 85 distally through knife slot 48 and into the knife channel 58.

In some embodiments, the knife actuation mechanism 90 may be positioned relative to shaft member 14 different than the depiction of knife actuation mechanism 90 in FIG. 3. For example, if the knife actuation mechanism 90 as depicted in FIG. 3 is disposed substantially between shaft members 14 and 12, then in some embodiments, knife actuation mechanism 90 may be disposed on an opposing side of shaft member 14 such that shaft member 14 is disposed between knife actuation mechanism 90 and shaft member 12. In this scenario, shaft members 12, 14 may be alternatively configured to allow knife blade 85 to advance through longitudinal passageway 27 defined by raised portions 13a, 13b (e.g., via knife guide 86) and into knife channel 58. For example, the distal ends 17, 19 of shaft members 12, 14, respectively, may be configured in various interlocking relationships (e.g., a lock-box configuration) that facilitate the knife 85 entering the knife channel 58 in various orientations relative to shaft members 12, 14 and/or knife channel 58.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A bipolar forceps, comprising:
 a mechanical forceps including first and second shafts each having a jaw member extending from a distal end thereof and a handle disposed at a proximal end thereof, the first and second shafts configured to rotate about a pivot for effecting movement of the jaw members relative to each other from a first position wherein the jaw members are disposed in spaced relation relative to one another to a second position wherein the jaw members cooperate to grasp tissue therebetween, wherein a portion of the first shaft is bifurcated to define a longitudinal slot;
 a longitudinal passageway defined through the pivot;
 a disposable housing configured to releasably couple to the first shaft such that the longitudinal slot defined by the bifurcated portion of the first shaft is disposed within the disposable housing;
 an electrode assembly having a first electrode releasably coupleable to the jaw member of the first shaft and a second electrode releasably coupleable to the jaw member of the second shaft, the first electrode and the second electrode adapted to connect to a source of electrosurgical energy to allow selective conduction of electrosurgical energy through the tissue grasped between the jaw members to effect a tissue seal;
 at least one of the first or second electrodes including a knife channel defined along a length thereof, the knife channel configured to receive a knife blade therethrough to cut the tissue grasped between the jaw members;
 a flexible tissue stop configured to prevent the tissue grasped between the jaw members from moving proximal thereto, the flexible tissue stop having a knife slot defined therethrough configured to align with the knife channel to receive the knife blade therethrough; and
 an actuation mechanism at least partially disposed within the disposable housing and configured to selectively advance the knife blade through the knife channel to cut the tissue grasped between the jaw members.

2. The bipolar forceps according to claim 1, wherein the flexible tissue stop is configured to expand and contract upon movement of the jaw members between the first and second positions.

3. The bipolar forceps according to claim 1, wherein the longitudinal passageway is configured to longitudinally align with the knife slot defined through the flexible tissue stop when the jaw members are in the second position.

4. The bipolar forceps according to claim 1, further comprising a knife guide supported in the disposable housing and including a longitudinal knife slot defined therethrough that receives the knife blade therein.

5. The bipolar forceps according to claim 4, wherein the longitudinal knife slot defined through the knife guide is configured to longitudinally align with the knife slot defined through the flexible tissue stop when the jaw members are in the second position.

6. The bipolar forceps according to claim 1, further comprising a knife lockout mechanism configured to prohibit advancement of the knife blade into the knife channel when the jaw members are in the first position.

7. A bipolar forceps, comprising:
   first and second shafts each having a jaw member disposed at a distal end thereof, wherein a portion of the first shaft is bifurcated to define a longitudinal slot;
   a longitudinal passageway defined through a pivot about which the first and second shafts rotate to effect movement of the jaw members relative to each other;
   a disposable housing configured to releasably couple to the first shaft such that the longitudinal slot defined by the bifurcated portion of the first shaft is disposed within the disposable housing;
   a first electrode releasably coupleable to the jaw member of the first shaft and a second electrode releasably coupleable to the jaw member of the second shaft;
   a knife channel extending though at least one of the first or second electrodes and configured to receive a knife blade to cut tissue grasped between the jaw members; and
   a flexible tissue stop configured to prevent proximal movement of the tissue grasped between the jaw members.

8. The bipolar forceps according to claim 7, wherein the flexible tissue stop defines a knife slot configured to align with the knife channel to receive the knife blade therethrough.

9. The bipolar forceps according to claim 7, further comprising an actuation mechanism at least partially disposed within the disposable housing and configured to move through the longitudinal slot defined by the bifurcated portion of the first shaft to advance the knife blade through the knife channel to cut the tissue.

10. An electrosurgical forceps, comprising:
    first and second shafts each having a jaw member disposed at a distal end thereof, the first and second shafts configured to rotate about a pivot to effect movement of the jaw members relative to each other, the first shaft including a bifurcated portion defining a longitudinal slot;
    a disposable housing configured to releasably couple to the first shaft such that the longitudinal slot defined by the bifurcated portion of the first shaft is disposed within the disposable housing;
    a first electrode releasably coupleable to the jaw member of the first shaft and a second electrode releasably coupleable to the jaw member of the second shaft; and
    a tissue stop configured to prevent proximal movement of tissue grasped between the jaw members.

11. The electrosurgical forceps according to claim 10, further comprising an actuation mechanism at least partially disposed within the disposable housing and configured to move through the longitudinal slot defined by the bifurcated portion of the first shaft to advance a knife blade to cut the tissue grasped between the jaw members.

* * * * *